United States Patent [19]

Larock

[11] 4,279,823

[45] Jul. 21, 1981

[54] THALLATION CARBONYLATION OF ARENES

[75] Inventor: Richard C. Larock, Ames, Iowa

[73] Assignee: Iowa State University Research Foundation, Inc., Ames, Iowa

[21] Appl. No.: 102,567

[22] Filed: Dec. 11, 1979

[51] Int. Cl.³ .................. C07D 307/83; C07D 311/00
[52] U.S. Cl. ............................... 260/343.21; 544/92; 544/94; 260/326 R; 260/343.3 R; 260/346.7; 560/97; 560/103; 562/406
[58] Field of Search ............... 560/97, 103; 260/343.4, 260/343.47, 346.7, 343.3 R, 343.21; 544/94, 92

[56] References Cited

U.S. PATENT DOCUMENTS

| | | | |
|---|---|---|---|
| 2,680,751 | 6/1954 | Prichard | 260/346.7 |
| 3,745,173 | 7/1973 | Henry | 560/97 X |
| 3,790,607 | 2/1974 | Lichstein | 560/103 |
| 3,832,381 | 8/1974 | Taylor et al. | 260/343.21 X |
| 3,917,670 | 11/1975 | Baird, Jr. et al. | 560/103 X |
| 4,093,647 | 6/1978 | Van Venrooy | 562/406 |

OTHER PUBLICATIONS

Taylor et al., J. Am. Chem. Soc., vol. 93, pp. 4895–4850 (1971).
Mori et al., Heterocycles, vol. 13, pp. 329 to 332 (1979).
Falbe, Carbon Monoxide in Organic Synthesis, frontispage, pp. VIII–IX, 82–83 and 98–99, Springer-Verlag, N.Y. (1970).
Davidson et al., J. Chem. Soc. (A), 1968, pp. 1616 to 1617.

*Primary Examiner*—John D. Randolph
*Attorney, Agent, or Firm*—Zarley, McKee, Thomte, Voorhees & Sease

[57] ABSTRACT

Simple arenes, aryl alcohols, aryl acids and aryl amides are reacted with an electrophilic thallium salt to provide arylthallium intermediates; and thereafter, the arylthallium compound is directly carbonylated by reacting with carbon monoxide in the presence of a noble metal carbonylation catalyst, such as palladium halide salts. The carbonylation reaction provides an excellent yield at room temperature and atmospheric pressure and is catalytic with respect to the noble metal salt.

10 Claims, No Drawings

THALLATION CARBONYLATION OF ARENES

GRANT REFERENCE

The invention described herein was made in the course of work under a grant or award from the Department of Health, Education and Welfare.

BACKGROUND OF THE INVENTION

In recent years a substantial number of important new synthetic procedures have been developed utilizing organothallium intermediates. Carbonylation of arylthallium compounds should provide a useful, direct and simple method of synthesis of a wide variety of biologically active compounds such as the lactones, phthalides, as well as anhydrides such as phthalic anhydride. In addition, various phthalide derivatives have shown useful fungicidal, bacteriocidal, herbicidal and analgesic activity. Some have even been reported as useful in treating heart disease, while other derivatives show diuretic and hypotensive-hypertensive activity.

Until recently, most of the synthetic routes to these types of compounds started with the carboxylic acid, corresponding to the lactone-carbonyl group and then introduced an orthoside chain which rapidly lactonized. But the yields were unsatisfactory and oftentimes side reactions occurred. Also, many of the starting materials were not readily available.

Direct carbonylation of arylthallium compounds has been studied and reported. See for example, Davidson, J. M., et al., *J. Chem. Soc.* A. 1968, pp. 616–617. However, the procedure as reported requires very stringent conditions of high temperature and pressure; in particular pressures of from 90 to 250 atmospheres at temperatures of 75° F. to 135° F. And even then, the reported yields are quite low. It therefore can be seen that there is not currently a method for direct carbonylation of arylthallium compounds at moderate temperatures and pressures to provide a direct and convenient synthesis route for a wide variety of biologically active compounds, including phthalides, 3,4-dihydroisocoumarins, anhydrides such as phthalic anhydride, and the like.

This invention has as its primary object the fulfillment of this need. The manner of accomplishing this objective as well as others will become apparent from the detailed description of the invention which will follow hereinafter.

SUMMARY OF THE INVENTION

The direct carbonylation of arylthallium compounds under ambient conditions has been accomplished by insertion of carbon monoxide into the arylthallium compound simply by employing catalytic amounts of noble metal carbonylation catalysts, such as palladium chloride. The reaction is direct, of low energy consumption since it can be run at ambient conditions, and is catalytic with respect to the noble metal catalysts used for the carbonylation. Additionally, the starting materials are readily available.

DETAILED DESCRIPTION OF THE INVENTION

For convenience of description, an equation representing the overall two step reaction, that is, the first step thallation reaction to provide a thallated intermediate, followed by carbonylation in the presence of a noble metal catalyst, is set forth in equation format. In the equations which follow "Ar" represents any arene.

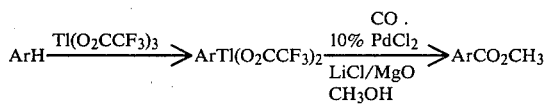

As can be seen from an examination of the above presented equation, in accordance with the first step, an arene, or in other words an aromatic compound, is reacted with an electrophilic thallium salt in the presence of an organic solvent to provide thallation of the arene to give an arylthallium intermediate compound.

Of course, the precise arene used in this initial thallation reaction will control the ultimate end product. That is to say, if a compound such as benzene or any other unsubstituted arene is employed, assuming an alcohol solvent for the system, the end product will be an ester. If an aryl alcohol is used, the end product will be a lactone, such as a phthalide or 3,4-dihydroisocoumarin. If an aryl acid, such as benzoic acid, is used, the end product will be an anhydride, such as phthalic anhydride. And finally, if the product is an amide, the end product will be an aryl imide.

The precise arene employed is not critical. Of course, what determines the starting aromatic compound is the desired carbonylated compound being synthesized. Satisfactory results have been attained when the starting compounds are simple arenes, aryl alcohols, aryl acids and aryl amides. Generally, the most satisfactory results are achieved when the arene compound is a $C_{12}$ or less structure and most preferably a $C_6$ to $C_{12}$ structure. Desirably the aromatic ring should not be deactivated by very many substituted electron withdrawing substituents which would make it non-reactive towards thallation. Examples of such electron withdrawing groups are, among others, nitro groups, cyano groups, sulfonic acid groups, ester groups and acid groups. The electrophilic thallium salt employed is not critical the essential factor simply being that the anion must be one which tends to make the thallium ion sufficiently active with respect to the substituents on the aromatic ring. Suitable anions have been found to be trifluoroacetate, perchlorate, nitrate and acetate. Because of the ease of formation and availability, it is preferred that the electrophilic thallium compound be thallium trifluoroacetate. For details with respect to preparation of thallium trifluoroacetate, see, McKillop, et al. *J. Am. Chem. Soc.*, Vol. 93, p. 4841–4844 (1971) which is incorporated herein by reference. The solvent employed in this first reaction step is not critical, and generally may be any solvent which will suitably dissolve the thallium compound and the starting aromatic compound. Suitable solvents are preferably polar solvents such as trifluoroacetic acid, tetrahydrofuran, and acetic acid, or less polar solvents such as ether, methylene chloride and chloroform. Of course, others may also be employed conveniently.

The reaction temperature and pressure are not critical factors. Generally, the reaction may be run at any temperature from −20° C. up to 100° C., with ambient temperature being satisfactory. The reaction time varies depending upon the activity of the starting aromatic compound and can be from a mere few minutes, up to as long as 48 hours. Commonly, a twelve hour thallation reaction time is more than sufficient.

Examples of suitable aromatic compounds falling within the general category previously set forth which can be successfully thallated, followed by direct carbonylation, include benzylic and β-phenethyl alcohols, benzoic and phenylacetic acids, benzamide and acetanilide.

As will be apparent from the examples below, if the starting aromatic compound has substituents on the aryl group, it is preferred that these substituents be activating groups such as hydroxyl, acyloxy, alkyl, and/or nitrogen containing groups, such as amines.

After the initial formation of the aryl thallium intermediate compound, if desired, the solvent may be stripped off by a vacuum stripping operation. It is, however, not necessary to even isolate the intermediate unless one has a specific desire to do so. If isolation of the intermediate is not deemed important, the reaction can directly proceed to the carbonylation step.

In the carbonylation step, the arylthallium intermediate is involved in an exchange with the noble metal carbonylation catalyst, followed by addition of the carbonyl group and regeneration of the noble metal catalyst.

This carbonylation reaction is conducted in a carbon monoxide atmosphere which is provided, simply by flushing the system with carbon monoxide during the reaction.

The noble metal carbonylation catalyst which may be employed in catalytic quantities, may for example, be salts of palladium, platinum, iridium, rhodium, ruthenium and the like. Preferably the salts are halide salts and preferably the noble metal is palladium. And most preferably, the reaction is conducted in the presence of palladium chloride. It has also been found effective that the reaction be conducted in the presence of an alkali metal halide. Most preferably, the additional salt is a lithium salt and, specifically, lithium chloride. The amount of the noble metal salt, preferably a palladium chloride salt, which may be employed, can vary from about 1% of an equivalent in comparison with the aromatic compound, up to about 10% of an equivalent. No particular advantage is obtained by using more than 10% of an equivalent amount, although the reaction can be conducted in the presence of equivalent amounts if one desires to do so.

It has also been found desirable to add magnesium oxide salt to some of the reactions in order to increase yields. It is believed that the addition of magnesium oxide increases the reaction yield by reacting with any excess acid which might be formed during the reaction. Very importantly, as will be readily seen from the examples which will follow hereinafter, the direct carbonylation reaction is conducted at ambient conditions. That is to say, temperature and pressure are not critical, and reaction can be conveniently run at room temperature and atmospheric pressure.

Again, time does not appear to be an important factor with respect to the carbonylation reaction, and it seems to occur within a few minutes; however, in most instances the reaction has been allowed to run overnight to assure completion.

In the examples which follow hereinafter, a general standardized procedure was employed. The procedure will be described in detail with respect to example 3, forming phthalide, it being understood that the procedure is varied only with the precise materials employed, unless stated otherwise.

One mmol of aryl alcohol was thallated according to the published procedure, Taylor, E. C.; Kienzle, F.; Robey, R. L.; McKillop, A.; Hunt, J. D. *J. Am. Chem. Soc.* 1971, 93, 4845–4850 which is incorporated herein by reference, using a 1 M solution of thallic trifluoroacetate in trifluoroacetic acid [1–1.2 eq. $Tl(O_2CCF_3)_3$]. The procedure was modified for aryl alcohols with one or more activating groups on the ring by diluting the solution with 5 mL of tetrahydrofuran and stirring overnight at room temperature. The solvents were then removed under vacuum and the arylthallium intermediates carbonylated without further purification. Palladium chloride (0.1 mmol), anhydrous lithium chloride (2 mmol), magnesium oxide (2 mmol), and 5 ml methanol were placed in a round bottom flask with a septum inlet. The system was flushed with carbon monoxide and the arylthallium compound dissolved in 5 mL methanol was added, after which the system was again flushed with carbon monoxide and maintained under one atmosphere pressure. After the reaction had stirred overnight at room temperature, the product was isolated by standard extractive and recrystallization procedures, or the yield was determined by gas chromatography using an internal standard.

The following table shows Examples 1–12.

TABLE I

Thallation-Carbonylation of Arenes

| Example | Arene | Product | % Yield[a] |
|---------|-------|---------|------------|
| 1 | ⌬ | ⌬—$CO_2CH_3$ | 52 |
| 2 | $(CH_3)_3C$—⌬ | $(CH_3)_3C$—⌬—$CO_2CH_3$ | 80 |
| 3 | ⌬—OH | phthalide | 33 |
| 4 | $CH_3O$—⌬—OH | $CH_3O$—phthalide | 89(47) |

TABLE I-continued
Thallation-Carbonylation of Arenes

| Example | Arene | Product | % Yield[a] |
|---|---|---|---|
| 5 | HO-C6H4-CH2OH (meta) | 5-hydroxyphthalide | (95) |
| 6 | C6H5-CH2CH2OH | isochroman-1-one | 62 |
| 7 | cis-2-phenylcyclohexanol | cis-fused tricyclic lactone | 88 |
| 8 | trans-2-phenylcyclohexanol | trans-fused tricyclic lactone | 77(13) |
| 9 | benzoic acid | phthalic anhydride | 44 |
| 10 | phenylacetic acid | homophthalic anhydride | (56) |
| 11 | benzamide | phthalimide | 83 |
| 12 | acetanilide | 2-methyl-4H-3,1-benzoxazin-4-one | (40) |

[a]Percent yield based on starting arene determined by gas chromatographic analysis using an internal standard (isolated, purified yield).

As can be seen, it is particularly noteworthy that only catalytic amounts of the noble metal catalyst, particularly palladium chloride are required, and that no additional reoxidant for the palladium need be added. The thallium (III) salt present in the reaction mixture serves this role.

The thallation-carbonylation sequence also provides a highly convenient route to a variety of aromatic lactones. For example, one can take advantage of the strong ortho directing effect of the oxygen atom in benzylic and β-phenethyl alcohols to afford orthothallated products readily carbonylated to phthalide and 3,4-dihydroisocoumarins, respectively (examples 3–8). Such lactones comprise a large class of naturally occurring, physiologically active compounds with interesting fungicidal, bacteriocidal, herbicidal, analgesic, diuretic and hypotensive-antihypertensive activity.

The results tabulated in the table indicate that benzylic alcohols possessing groups which activate the ring towards electrophilic aromatic substitution, give higher yields of phthalides and that β-phenethyl alcohols having alkyl groups on the side chain which hold the hydroxyl group in a more rigid conformation, give increased yields of 3,4-dihydroisocoumarins.

The reactions are also highly stereo- and regiospecific. Thus, thallation-carbonylation of cis- and trans-2-phenylcyclohexanoles (examples 7 and 8) provide exclusively the cis and trans fused tricyclic lactones respectively. Substituents on the aromatic ring are also observed to effect a very pronounced directive effect. For example, thallation-carbonylation of m-methoxybenzyl alcohol affords the 5-methoxyphthalide in 89% yield and only a trace of the 7-methoxyphthalide (example 4). Similarly, m-hydroxybenzyl alcohol affords a 95% isolated yield of pure 5-hydroxyphthalide (example 5).

Further, this thallation-carbonylation procedure has proven to be quite general for a variety of other aromatic compounds as well. Thus, thallation-carbonylation of benzoic and phenylacetic acids yields phthalic and homophthalic anhydrides, respectively (examples 9 and 10) and benzamide affords phthalimide in excellent yield (example 11). In similar fashion, acetanilide is cyclocarbonylated to acetylanthranil (example 12). Thus, the versatility of this procedure proves its usefulness in the synthesis of a large variety of interesting heterocyclic systems.

It has also been found that the best results are obtained when from 1.0 to 1.2 equivalents of the electrophilic thallium salt are used per equivalent of aromatic compound.

What is claimed is:

1. A process of synthesis of certain five membered ring lactones and six membered ring lactones of the formula:

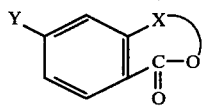

said method comprising reacting an aryl alcohol of the formula:

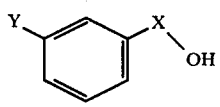

with an electrophilic thallium salt in the presence of an organic solvent for said reactants to provide an arylthallium intermediate compound; and carbonylating under a substantially ambient pressure and temperature, said arylthallium compound by reacting with carbon monoxide in the presence of an inorganic alkali metal halide salt and magnesium oxide and a catalytically effective amount of noble metal carbonylation catalysts to provide said lactones, with Y being the same in both the starting aryl alcohol and the lactone, and being selected in each instance from the group of hydrogen, methoxy and hydroxy, with X being selected from the group consisting of methylene, dimethylene, cis-cyclohexyl and trans-cyclohexyl.

2. The process of claim 1 wherein said electrophilic thallium salt is one, the anion of which tends to make the thallium ion more active with respect to the substituents on the aromatic ring.

3. The process of claim 2 wherein said anion is selected from the group consisting of trifluoroacetate, perchlorate, nitrate and acetate.

4. The process of claim 3 wherein said solvent is selected from the group consisting of trifluoroacetic acid, tetrahydrofuran, acetic acid, ether, methylene chloride and chloroform.

5. The process of claim 1 wherein said salt is a lithium salt.

6. The process of claim 5 wherein said salt is lithium chloride.

7. The process of claim 1 wherein said noble metal catalyst is a noble metal salt.

8. The process of claim 7 wherein said noble metal salt is a palladium halide.

9. The process of claim 8 wherein said noble metal salt is palladium chloride.

10. The process of claim 8 wherein the amount of noble metal salt is from about 1% to about 10% by equivalent weight of said aromatic compound.

* * * * *